US007857779B2

(12) United States Patent
Gondringer

(10) Patent No.: US 7,857,779 B2
(45) Date of Patent: Dec. 28, 2010

(54) TRACTION DEVICE FOR USE IN SURGERY

(76) Inventor: Chad J. Gondringer, 2431 S. 74th St., Lincoln, NE (US) 68506

( * ) Notice: Subject to any disclaimer, the term of this patent is extended or adjusted under 35 U.S.C. 154(b) by 290 days.

(21) Appl. No.: 12/074,791

(22) Filed: Mar. 6, 2008

(65) Prior Publication Data
US 2009/0227929 A1  Sep. 10, 2009

(51) Int. Cl.
*A61F 5/00* (2006.01)
*A61F 5/37* (2006.01)
*A47B 7/00* (2006.01)
*A61B 1/00* (2006.01)

(52) U.S. Cl. .................. 602/33; 128/878; 5/621; 482/43

(58) Field of Classification Search ............ 602/31–36; 5/621, 600, 630, 690, 944, 948; 248/118; 128/878, 877, 845, 882, 897, 898; 606/198, 606/191, 185, 130, 201; 482/23, 43, 54, 482/69, 904
See application file for complete search history.

(56) References Cited

U.S. PATENT DOCUMENTS

| | | | |
|---|---|---|---|
| 2,590,739 A | | 3/1952 | Wagner et al. |
| 3,710,787 A | * | 1/1973 | Rabjohn .................. 602/32 |
| 4,236,265 A | * | 12/1980 | Carradine ................ 5/630 |
| 4,807,618 A | | 2/1989 | Auchinleck et al. |
| 4,828,453 A | | 5/1989 | Martin et al. |
| 4,930,523 A | | 6/1990 | Laico et al. |
| 4,941,464 A | | 7/1990 | Scott |
| 5,275,176 A | | 1/1994 | Chandler |
| 5,667,461 A | * | 9/1997 | Hall ...................... 482/69 |
| 5,785,057 A | | 7/1998 | Fischer |
| 5,926,876 A | | 7/1999 | Haigh et al. |
| 5,961,512 A | | 10/1999 | Purnell |
| 6,564,406 B2 | | 5/2003 | VanSteenburg et al. |
| 6,704,959 B2 | | 3/2004 | Schuerch |
| 6,895,969 B2 | | 5/2005 | Malcolm et al. |
| 7,243,654 B2 | | 7/2007 | Schuerch |

* cited by examiner

*Primary Examiner*—Patricia M Bianco
*Assistant Examiner*—Tarla R Patel
(74) *Attorney, Agent, or Firm*—Dennis L. Thomte; Thomte Patent Law Office LLC

(57) ABSTRACT

A traction device for use in surgery is disclosed with the traction device being secured to one side of a surgical table. The traction device includes one or more traction lines which include a line-tensioning device at one end thereof and a connector at the other end thereof for attachment to the limb of a patient undergoing surgery. A tension meter is associated with each of the traction or lines with the tension meter being connected to a readout which indicates the tension or traction force being imposed in the traction line. The traction device may be used for patients undergoing shoulder surgery or other types of limb surgery.

11 Claims, 5 Drawing Sheets

TRACTION DEVICE FOR USE IN SURGERY

BACKGROUND OF THE INVENTION

1. Field of the Invention

This invention relates to a traction device for surgery and more particularly to a traction device which is mounted at one side of a surgical table and which includes at least one line or cable which is attached to a limb of the patient undergoing surgery. Even more particularly, the invention includes a winch-like device for applying variable amounts of traction force to the cable. Even more particularly, the invention includes a tension meter which is operatively attached to the traction cable for sensing the amount of traction force in the traction cable.

2. Description of the Related Art

Traction devices such as those illustrated in U.S. Pat. Nos. 4,616,637; 4,930,523; and 5,961,512 are commonly used to apply traction to a person's shoulder during surgery thereof. All of the devices of the above-identified patents involve the use of weights which hang from the end of a traction cable or the like which is operatively connected to the patient's arm to apply traction to the patient's shoulder. Usually, those weights hang from the traction cable at a location near the surgical table. Frequently, the hanging weights are "bumped" by a member of the medical staff which creates a significant effect on the traction cable. Further, the amount of traction force in the traction cable or cables can only be adjusted by the addition or removal of weights suspended from the traction cable. The weights themselves are inconvenient to store.

Additionally, the supporting framework of the traction devices of the prior art are normally quite cumbersome and involve many component parts. Further, the supporting framework of the prior art devices do not lend themselves to proper orientation thereof with respect to the patient and are not believed to be able to apply different amounts of traction force to different parts of the arm or limb to which traction is being applied.

SUMMARY OF THE INVENTION

A traction device is provided for use with a surgical table for supporting a patient during shoulder surgery. As will be described hereinafter, the traction device of this invention may also be used for applying traction to limbs of the patient during surgery other than shoulder surgery.

The traction device of this invention includes a generally inverted L-shaped frame means including an upstanding first frame portion, having upper and lower ends, and a generally horizontal extending second frame portion having inner and outer ends. The lower end of the first frame portion is selectively rotatably secured to the surgical table about a vertical axis. A first elongated hollow frame member, having inner and outer ends, is secured to the second frame portion and extends generally horizontally therefrom. A second elongated hollow frame member, having inner and outer ends, is secured to the second frame portion and extends generally horizontally therefrom. The outer end of the first frame member is disposed outwardly of the inner end of the second frame member.

The device further includes an inverted L-shaped third hollow frame member which is secured to the first frame portion and which includes a generally vertically extending portion and a generally horizontally extending portion having inner and outer ends. A first pulley is rotatably mounted at the outer end of the first frame member about a horizontal axis and a second pulley is rotatably mounted at the outer end of the second frame member about a horizontal axis. A third pulley is rotatably mounted at the outer end of the generally horizontal extending portion of the third frame member about a horizontal axis.

A first support or traction line, having inner and outer ends, is movably positioned in the first frame member and has its outer end extending outwardly from the outer end of the first frame member and which passes over the first pulley and then downwardly therefrom. A second support or traction line, having inner and outer ends, is movably positioned in the second frame member and has its outer end extending outwardly from the outer end of the second frame member and which passes over the second pulley and then downwardly therefrom. A third support or traction line, having inner and outer ends, is movably positioned in the third frame member and has its outer end extending outwardly from the outer end of the horizontal extending portion of the third frame member and which passes over the third pulley and then downwardly therefrom.

First, second and third line-tensioning devices are secured to the first, second and third support lines. The outer ends of the first, second and third support lines are adapted to be secured to the arm of a patient undergoing shoulder surgery. If the traction device is being used during surgical procedures other than shoulder surgery, one or more of the support lines would be secured to the patient's limb requiring traction.

Preferably, the first and second frame members are length adjustable and the generally vertically extending portion of the third frame member is vertically adjustable. A tension meter is associated with each of the first, second and third support lines which senses the tension or traction force therein respectively. The first, second and third tension meters are connected to a tension read-out device mounted on the traction device which indicates the tension or traction force in the support lines.

It is, therefore, a principal object of the invention to provide a traction device for use with a surgical table for supporting a limb of a patient during surgery.

A further object of the invention is to provide a traction device for use with a surgical table for supporting a patient during shoulder surgery and which applies traction force to the patient's arm of the shoulder undergoing surgery.

A further object of the invention is to provide a traction device which is removably supported at one side of a surgical table and which is easily adjustable to properly support the patient's arm or limb.

Still another object of the invention is to provide a traction device for use with a surgical table which includes one or more traction lines or cables which are attached to the patient and which have tension meters associated therewith for indicating the tension in the traction line or lines.

Still another object of the invention is to provide a traction device for use of the surgical table wherein line-tensioning devices are attached to each of the traction lines for adjusting the tension or traction force therein.

Still another object of the invention is to provide an invention of the type described which eliminates the use of hanging weights.

These and other objects will be apparent to those skilled in the art.

A BRIEF DESCRIPTION OF THE DRAWINGS

DESCRIPTION OF THE PREFERRED EMBODIMENT

Figure 1:
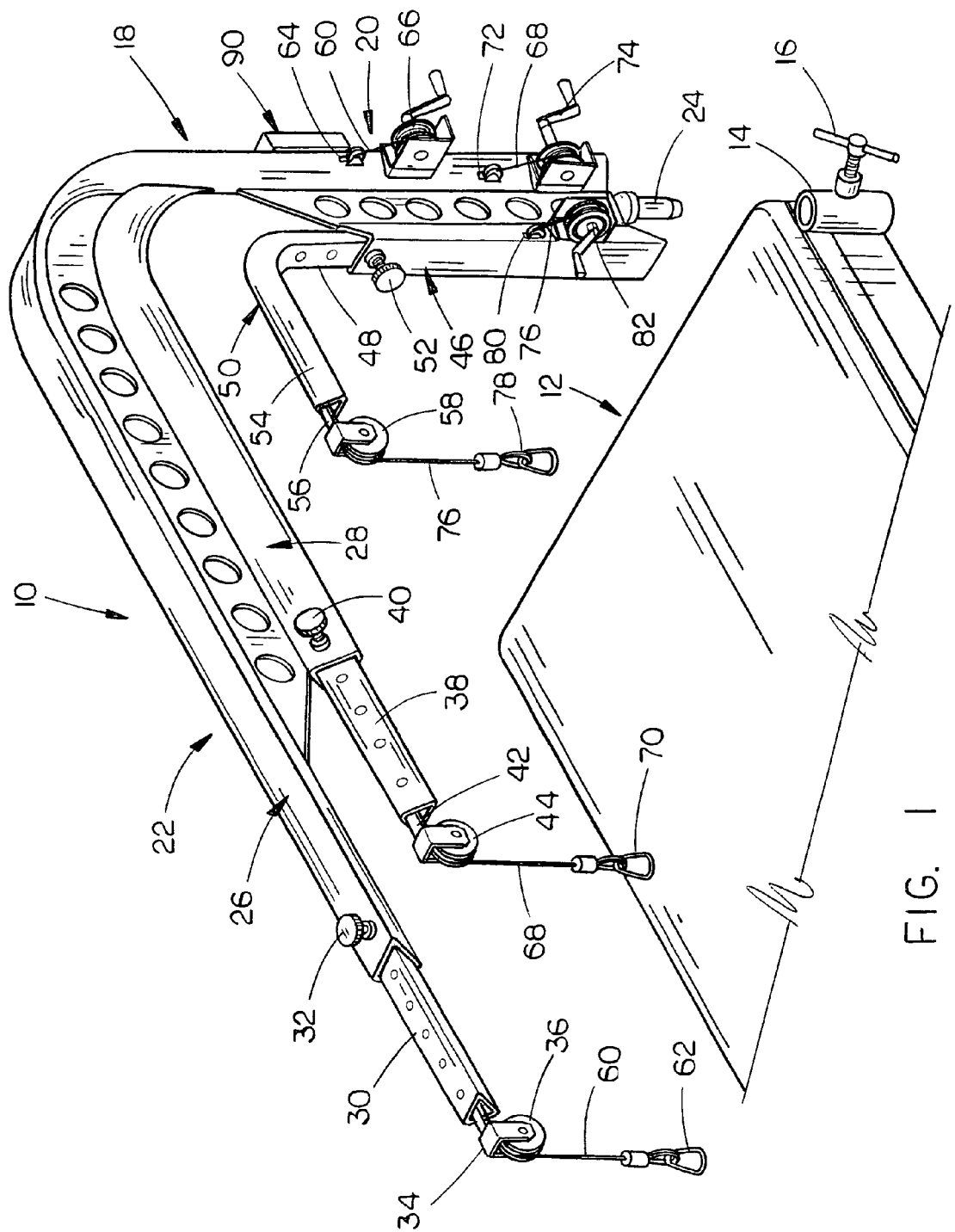
FIG. 1 is a perspective view of the traction device of this invention which illustrates the manner in which the device may be attached to a surgical table.
Figure 2:
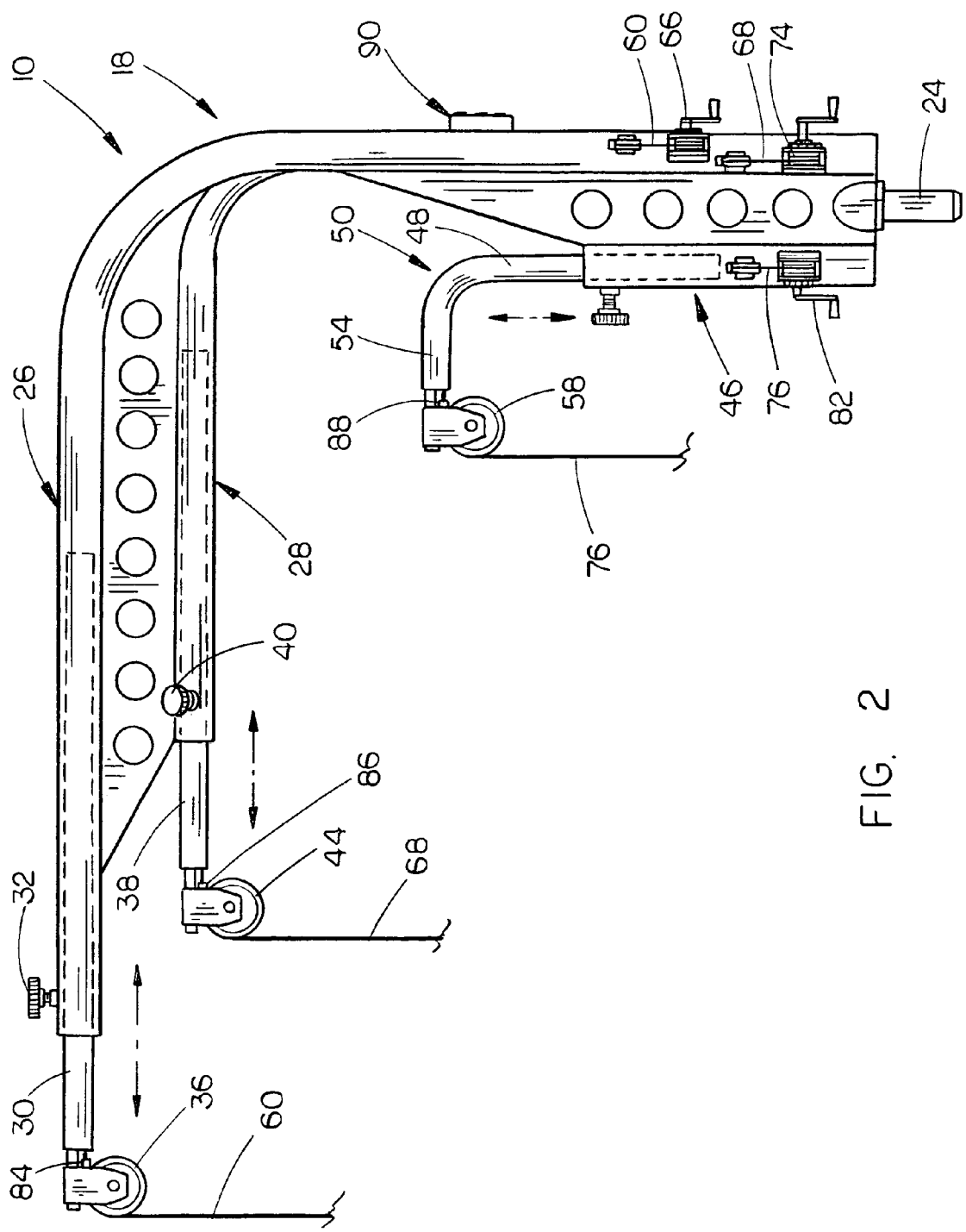
FIG. 2 is a side elevational view of the device of FIG. 1.
Figure 3:
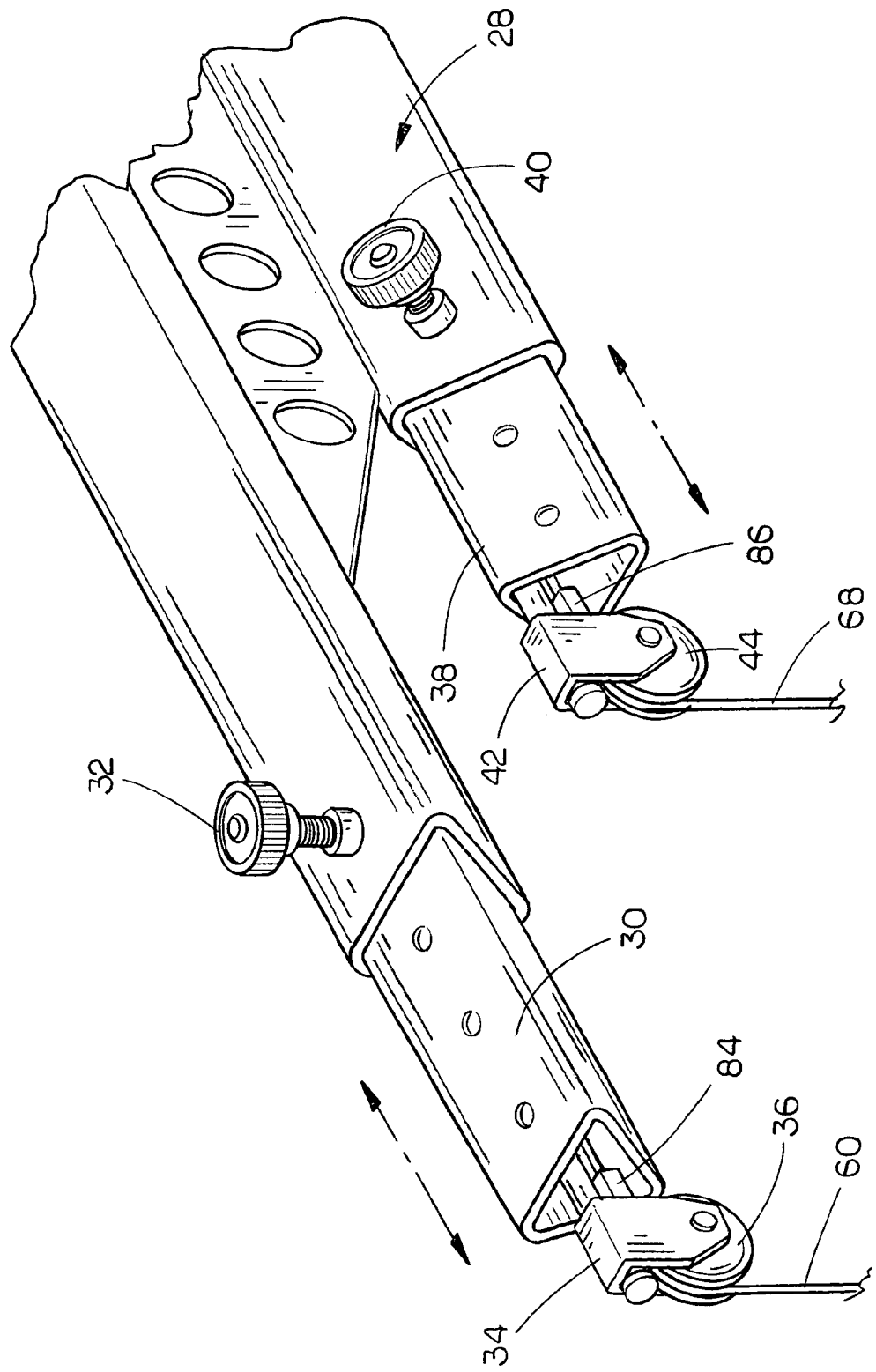
FIG. 3 is a partial perspective view of a portion of the action device.
Figure 4:
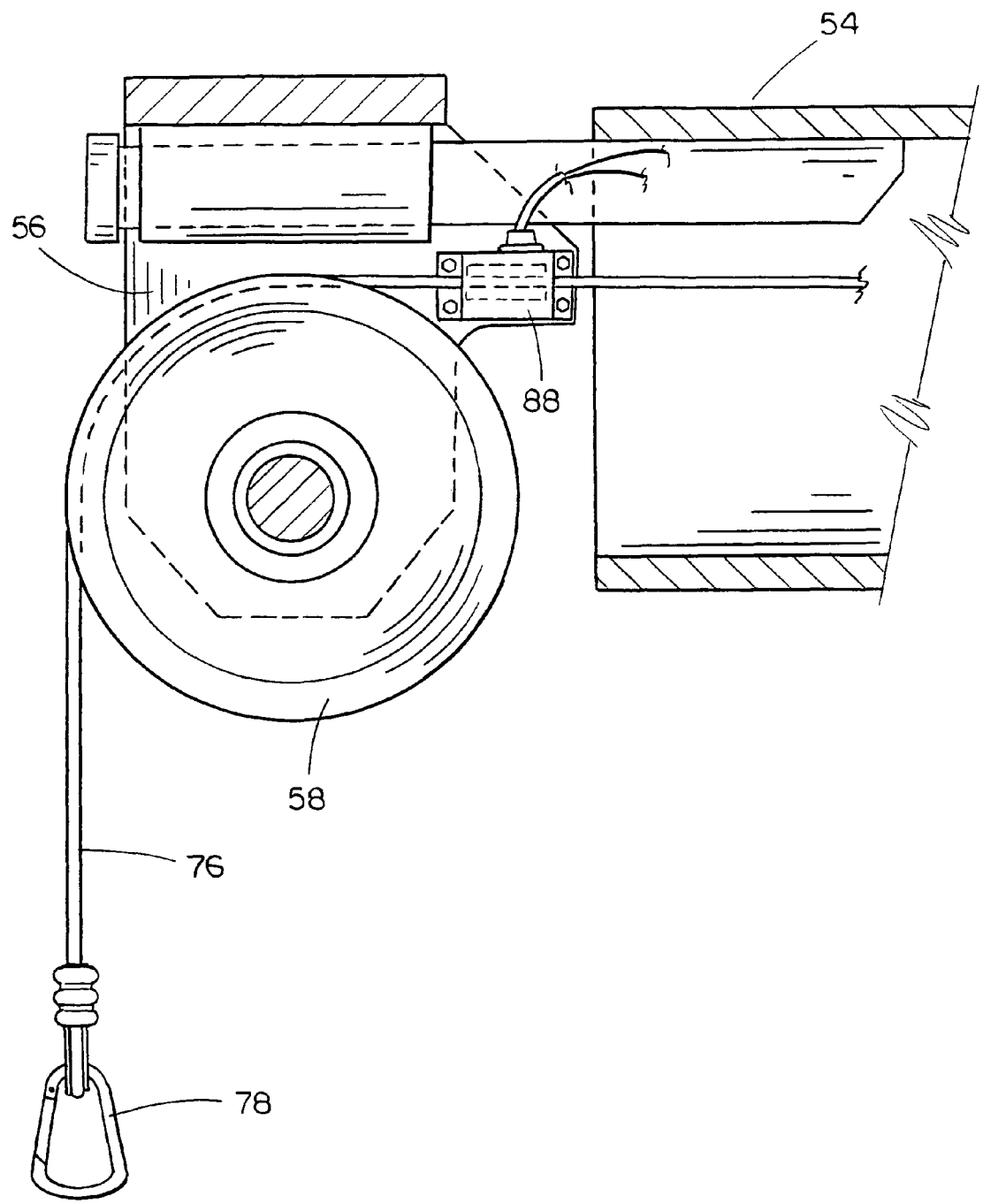
FIG. 4 is a partial side view of a portion of the action device with portions thereof cut away to more fully illustrate the invention.
Figure 5:
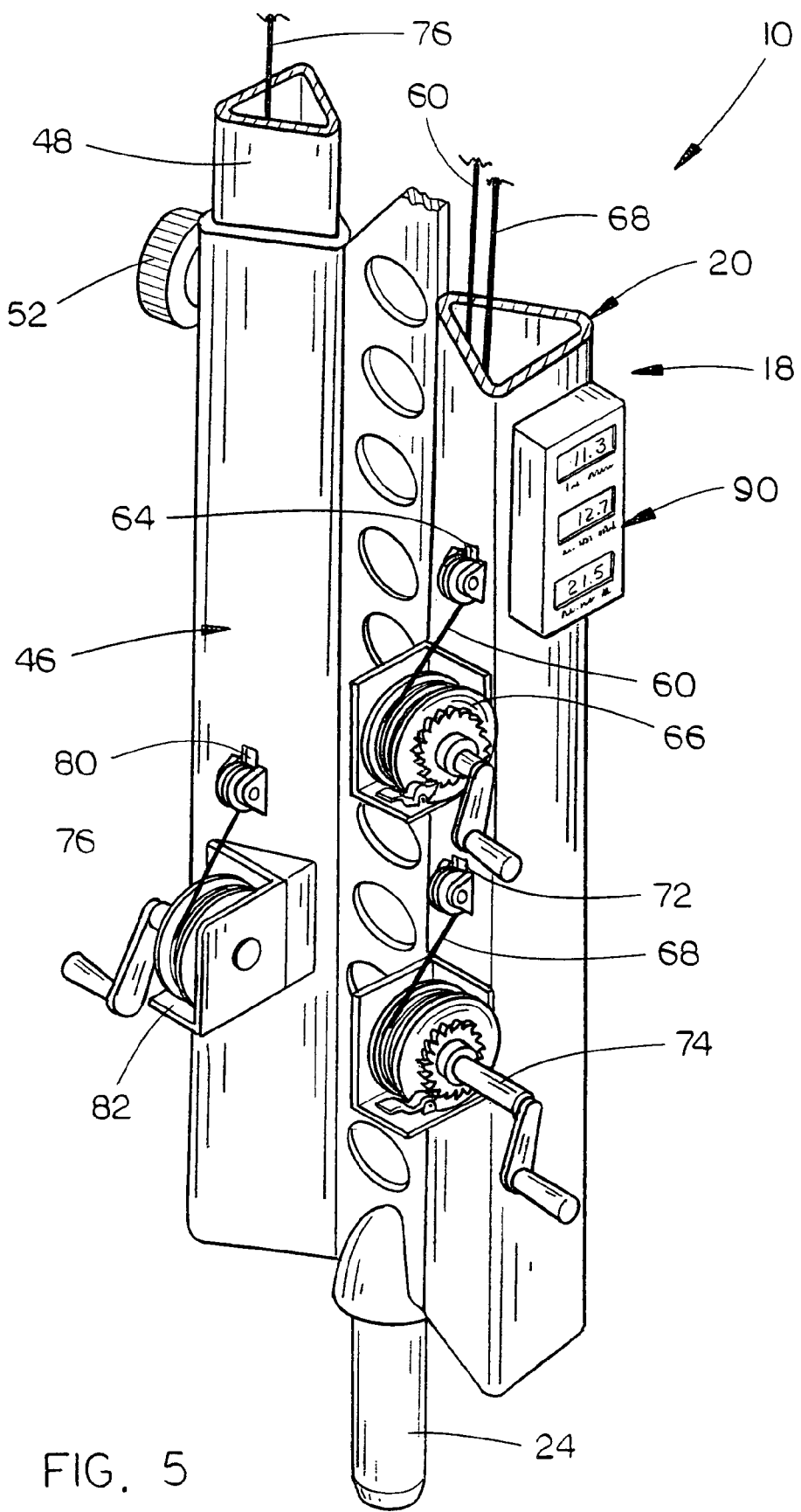
FIG. 5 is a partial perspective view of the lower end of the traction device.

The traction device of this invention is referred to generally by the reference numeral 10 while the numeral 12 refers to a conventional surgical table which includes a tubular support 14 at one side thereof and which includes a threaded locking device 16. Traction device 10 includes a generally inverted L-shape frame means 18 including an upstanding first frame portion 20 and a generally horizontally extending second frame portion 22. For purposes of description, the first frame portion 20 will be described as having upper and lower ends while the second frame portion will be described as having inner and outer ends. The lower end of first frame portion 20 has a downwardly extending plug for the light 24 which is adapted to be received within the tubular support 14 and maintained in various rotatable positioned with respect thereto by the locking device 16.

The second frame portion 22 includes a first elongated frame member 26, having inner and outer ends, and which extends horizontally from the first frame portion. The second frame portion 22 also includes a second elongated frame member 28 which extends generally horizontally from the first frame portion. As seen in FIG. 1, the outer end of the first frame member 26 is disposed outwardly of the inner end of the second frame member 28.

Frame member 30 is selectively slideably received within the frame member 26 and is held in various positions with respect thereto by thumbscrew 32. A pulley support 34 is secured to the outer end of the frame member 30 and has a pulley 36 secured thereto which is rotatable about a horizontal axis.

An elongated frame member 38 is adjustably telescopically or slideably received within frame member 28 and is held in various positions with respect thereto by thumbscrew 40. Pulley support 42 is secured to the outer end of frame member 38 and has a pulley 44 rotatably secured thereto about a horizontal axis.

First frame portion 20 includes a vertically extending frame member 46 which has upper and lower ends and which has the vertically extending portion 48 of a frame member 50 vertically adjustably mounted therein and which is held in various positions with respect thereto by thumb screw 52. Frame member 50 includes a horizontally extending portion 54 which has a pulley support 56 secured to the outer end thereof which has a pulley 58 rotatably secured thereto about a horizontal axis.

As seen, first frame portion 20 is hollow with the upper end thereof communicating with the inner ends of frame members 26 and 28. A traction cable or line 60 has a connector 62 secured to the outer end thereof and extends over pulley 36 and thence inwardly through frame member 30, thence inwardly through frame member 26 and thence downwardly through the interior of frame portion 20. The lower or inner end of line 60 exits from the frame portion 20 at 64 and is connected to a conventional winch including a ratchet means so that the desired amount of traction force may be applied to the line 60.

Traction cable or line 66 having a connector 70 at its outer end extends over pulley 44 and thence inwardly through frame member 38, through the interior of frame member 26 and then downwardly through the frame portion 20. Line 68 exits from frame portion 20 at 68 and is connected to a conventional ratchet type winch 74 adapted to apply the desired amount of traction force to the traction cable or line 68. Traction line or cable 76 having a connector 78 secured to the outer end thereof extends over pulley 58, thence inwardly through the horizontal extending portion 54 of frame member 50, thence downwardly through the vertically extending portion 48 of frame member 50 and thence downwardly through frame member 46. The traction cable or line 76 exits from the frame member 46 at 80 and has a conventional ratchet-type winch 82 secured thereto for exerting the desired amount of traction force to the line 76. Traction cables or lines 60, 68 and 76 have tension meters 84, 86 and 88 associated therewith which sense the tension in lines 60, 68 and 76 respectively. The tension meters 84, 86 and 88 are conventional in design and are readily available from such companies as Tensitron, Inc., 733 South Bowden Street, Longmont, Colo. 80501 or Penn-Tech International, 306 Westown Road, West Chester, Pa. 19382. One type of tension meter is also described in U.S. Pat. No. 4,587,855. The tension meters 84, 86 and 88 are electronically connected to a digital readout device 90 of conventional design which is secured to the first frame portion 20 for indicating the tension (traction force) in each of the lines 60, 68 and 76.

Assuming that the device 10 is to be used during shoulder surgery, plug 24 of device 10 is inserted into the tubular member 14 and is rotatably moved to the desired position and locked in that position by locking device 16. The frame members 30 and 38 are horizontally adjustably positioned with respect to the frame members 26 and 28 and the frame member 48 is selectively vertically adjustably positioned with respect to the frame member 46. The connectors 62, 70 and 78 are then secured to the patient's arm in a conventional manner using conventional supports. The winches 66, 74 and 82 are individually operated until the proper amount of traction force or tension is created in the lines 60, 68 and 76 as indicated by the digital readout 70 as sensed by the tension meters, 84, 86 and 88 respectively. Thus, the desired amount of traction force may be applied to any of the cables 60, 68 and 76 in a precise manner as indicated by the readout 90. The device 10 of this invention eliminates the need for hanging weights which suffers from the disadvantages outlined above.

Although the design of the device 10 is shown in one form in the drawings, the device 10 could be constructed of a composite material and could have other cross-sectional configurations. Although the device 10 is ideally suited for use in supporting an arm of a patient during shoulder surgery, the device could incorporate one or more traction lines or cables having a tension meter associated therewith with a line-tensioning device associated therewith so that other limbs of the patient could be supported during surgery of a foot, ankle, leg, etc.

Thus it can be seen that the invention accomplishes at least all of its stated objectives.

The invention claimed is:

1. A patient support for use with a surgical table for supporting a patient during shoulder surgery, comprising:
    a generally inverted L-shaped frame means including an upstanding first frame portion, having upper and lower ends, and a generally horizontally extending second frame portion having inner and outer ends;

said lower end of said first frame portion being selectively rotatably secured to the surgical table about a vertical axis;

a first elongated tubular frame member, having inner and outer ends, and extending generally horizontally from the first frame portion;

a second elongated tubular frame member, having inner and outer ends, and extending generally horizontally from the first frame portion below said first tubular elongated frame member;

said outer end of said first frame member being disposed outwardly of said outer end of said second frame member;

an inverted L-shaped third frame member secured to said first frame portion and including a generally vertically extending portion and a generally horizontally extending portion having inner and outer ends;

said generally horizontally extending portion of said third frame member being disposed below said second elongated frame member;

a fourth frame member slidably adjustably received in said outer end of said first frame member and having inner and outer ends;

a fifth frame member slidably adjustably received in said outer end of said second frame member and having inner and outer ends;

a first pulley rotatably mounted at the outer end of said fourth frame member about a horizontal axis;

a second pulley rotatably mounted at the outer end of said fifth frame member about a horizontal axis;

a third pulley rotatably mounted at the outer end of said generally horizontally extending portion of said third frame member;

a first support line, having inner and outer ends, movably positioned in said first frame member and said fourth frame member and having its outer end extending outwardly from said outer end of said fourth frame member and which passes over said first pulley and thence downwardly therefrom;

a second support line, having inner and outer ends, movably positioned in said second frame member and said fifth frame member and having its outer end extending outwardly from said outer end of said fifth frame member and which passes over said second pulley and thence downwardly therefrom;

a third support line, having inner and outer ends, movably positioned in said third frame member and having its outer end extending outwardly from said outer end of said horizontally extending portion of said third frame members and which passes over said third pulley and thence downwardly therefrom;

a first line-tensioning device secured to said first support line;

a second line-tensioning device secured to said second support line;

a third line-tensioning device secured to said third support line;

said outer ends of said first, second and third support lines adapts to be secured to the arm of a patient undergoing shoulder surgery.

2. The patient support of claim 1 wherein said generally vertically extending portion of said third frame member is vertically adjustable.

3. The patient support of claim 1 wherein a first tension meter is associated with said first support line which senses the tension therein.

4. The patient support of claim 1 wherein a second tension meter is associated with said second support line which senses the tension therein.

5. The patient support of claim 1 wherein a third tension meter is associated with said third support line which senses the tension therein.

6. The patient support of claim 1 wherein first, second and third tension meters are associated with said first, second and third support lines respectively.

7. The patient support of claim 6 wherein said first, second and third tension meters are connected to a tension read-out device which indicates the tension in said support lines.

8. The patient support of claim 1 wherein each of said line-tensioning devices comprises a rotatable winch.

9. The patient support of claim 1 wherein said vertically extending portion of said third frame member is vertically adjustable.

10. The patient support of claim 1 wherein portions of said first and second frame members are interconnected by a truss means.

11. The patient support of claim 1 wherein said third frame member is connected to said vertically extending portion of said L-shaped frame means by a truss means.

* * * * *